United States Patent [19]

Sullivan

[11] 4,080,558
[45] Mar. 21, 1978

[54] DEFIBRILLATOR BATTERY CHARGER

[75] Inventor: John William Sullivan, Mountain View, Calif.

[73] Assignee: Gould Inc., Chicago, Ill.

[21] Appl. No.: 664,974

[22] Filed: Mar. 8, 1976

Related U.S. Application Data

[63] Continuation of Ser. No. 537,126, Dec. 30, 1974, abandoned.

[51] Int. Cl.² .......................... H02J 7/00; A61N 1/00
[52] U.S. Cl. ................................ 320/39; 128/419 D; 307/66
[58] Field of Search ........................................ 320/2-5, 320/39, 40, 35, 36, 48; 307/65, 66, 69; 128/419 D, 419 PS

[56] References Cited

U.S. PATENT DOCUMENTS

| 3,157,870 | 11/1964 | Marino et al. ...................... 320/48 X |
| 3,258,013 | 6/1966 | Druz ................................ 128/419 D |
| 3,310,724 | 3/1967 | Grafham ........................ 320/DIG. 2 |
| 3,652,915 | 3/1972 | Eberts ................................. 320/35 X |
| 3,842,288 | 10/1974 | Bradshaw .......................... 320/39 X |

Primary Examiner—Robert J. Hickey
Attorney, Agent, or Firm—Flehr, Hohbach, Test, Albritton & Herbert

[57] ABSTRACT

Battery charger having means for delivering a trickle charge to maintain a difibrillator battery in a normally charged condition, switch actuated means for delivering a fast charge current to the battery, and means responsive to the battery voltage for supplying operating power to the defibrillator in the event that the battery voltage falls below a predetermined level whereby the charger will power the difibrillator directly in the event that the battery is unable to do so. The battery and defibrillator are protected from damage due to overcharging of the battery by interrupting the charging current in the event that the temperature of the battery exceeds a predetermined level or the voltage applied to the defibrillator reaches a predetermined level.

10 Claims, 1 Drawing Figure

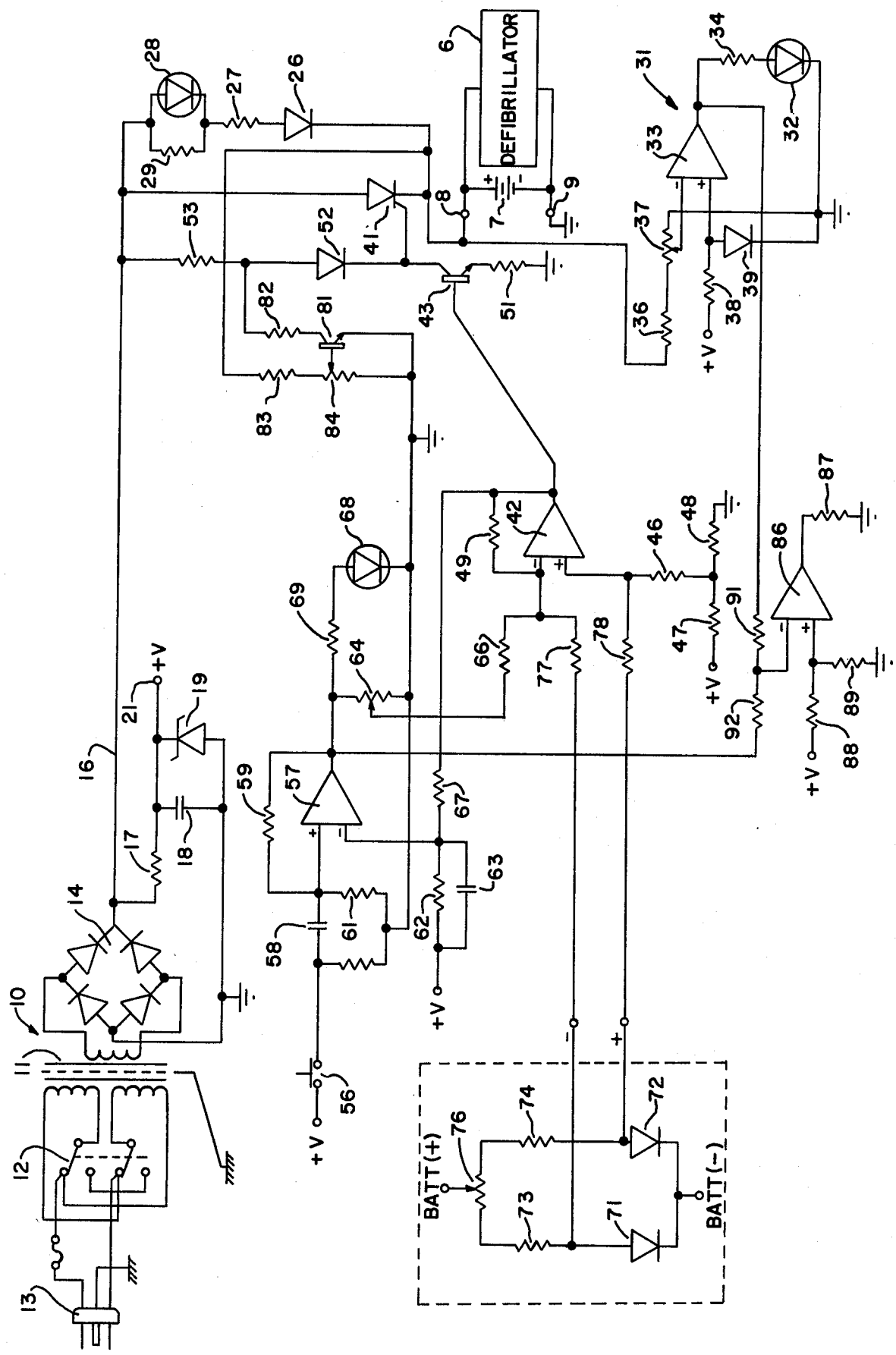

DEFIBRILLATOR BATTERY CHARGER

This is a continuation of application Ser. No. 537,126 filed Dec. 30, 1974, now abandoned.

BACKGROUND OF THE INVENTION

This invention pertains generally to medical equipment and more particularily to a battery charger for a defibrillator.

Heretofore, portable defibrillators have been provided for use in emergency situations and other applications away from a hospital or medical laboratory. Such defibrillators are generally powered by a battery or series of batteries which must be maintained in a charged condition to assure proper operation of the device.

Battery chargers heretofore utilized with portable defibrillators have included conventional trickle chargers for delivering a small charging current for maintaining the battery in a normally charged condition, and some chargers have also included a fast charge circuit for delivering a larger charging current for charging the battery rapidly in the event that it becomes discharged. Such fast charge circuits are generally manually actuated, and they can require as much as twenty minutes to recharge a good battery to a usable level. Such a charging time is not satisfactory in an emergency situation when a patient may begin to die in three minutes or less. Moreover, if the battery is not in good condition, the fast charge may receive it only briefly, and it may fail in an emergency situation.

SUMMARY AND OBJECTS OF THE INVENTION

In addition to a trickle charge mode and a fast charge mode, the battery charger of the invention includes means responsive to the voltage of the defibrillator battery for automatically supplying operating power directly to the defibrillator in the event that the battery voltage drops to a predetermined level. The charger also includes means responsive to the temperature of the battery for interrupting the fast charging current in the event that the temperature reaches a predetermined level. Means is also provided for interrupting the charging current in the event that the voltage applied to the defibrillator reaches a predetermined level.

It is in general an object of the invention to provide a new and improved battery charger for use with defibrillators.

Another object of the invention is to provide a battery charger of the above character which includes means for automatically supplying operating power to the defibrillator in the event that the defibrillator battery is unable to do so.

Another object of the invention is to provide a battery charger of the above character which includes means for protecting the battery and defibrillator from damage due to excessive charging of the battery.

Additional objects and features of the invention will be apparent from the following description in which the preferred embodiment is set forth in detail in conjunction with the accompanying drawing.

BRIEF DESCRIPTION OF THE DRAWING

The drawing is a schematic diagram of one embodiment of a battery charger according to the invention.

BRIEF DESCRIPTION OF THE PREFERRED EMBODIMENT

In the drawing, the battery charger is illustrated in connection with a defibrillator 6 and a battery 7. The battery is connected to the defibrillator for supplying power thereto, and the battery and defibrillator are connected to the battery charger by means of output terminals 8 and 9 on the charger. These termials can be of any suitable type, and they can, for example, include cables provided with suitable connectors for connection to the terminals of the battery. The battery can, for example, be a nickel-cadmium battery having a plurality of cells and an output voltage on the order of 26 to 28 volts when fully charged.

The battery charger includes a power supply 10 comprising a power transformer 11 having a pair of primary windings and a switch 12 for connecting the primary windings in parallel or series for operation from either 120 volts or 240 volts. A plug 13 is provided for connecting the charger to a conventional AC power system. A full-wave rectifier bridge 14 is connected to the secondary winding of transformer 11 and delivers an unfiltered voltage to a supply line 16. A filter consisting of a resistor 17 and a capacitor 18 and a voltage regulator consisting of a Zener diode 19 provide a regulated supply voltage $+V$ at an output terminal 21. In the preferred embodiment, the filtered voltage at terminal 21 has a peak value on the order of 24 volts.

Means is provided for applying a trickle charge to the battery from the power supply to maintain the battery in a charged condition. This means includes a diode 26 and a resistor 27 connected in series between supply line 16 and output terminal 8. An indicator consisting of a light emitting diode (LED) 28 and a resistor 29 is connected in series with the trickle charging circuit, and the LED is energized to provide a visual indication when the battery is receiving current through this circuit. The value of resistor 27 is selected to provide a trickle charge current on the order of 100 milliamperes with a normal line voltage of 120 volts and a maximum of 120 milliamperes with a line voltage of 130 volts.

A low voltage indicator 31 provides means for indicating when the battery voltage drops below a predetermined level. This indicator comprises a light emitting diode (LED) 32 which is connected to the output of an operational amplifier 33 by a resistor 34. A voltage proportional to the battery voltage is applied to the inverting input of op amp 33 by a voltage divider consisting of a fixed resistor 36 and a potentiometer 37. A reference voltage is applied to the non-inverting input of the op amp by a resistor 38 and diode 39. In the preferred embodiment, potentiometer 37 is adjusted so that LED 38 will be energized when the battery voltage is less than 21 volts.

A controlled switching device 41 is connected between supply line 16 and output terminal 8 for delivering a fast charge current to the battery and emergency operating power to the defibrillator. In the preferred embodiment, the switching device comprises a silicon controlled rectifier (SCR) 41 having its anode connected to the supply line and its cathode connected to the output terminal.

Means is provided for applying a control signal to the cathode gate of SCR 41 to maintain the SCR in a normally non-conductive state. This means includes an operational amplifier 42 and transistor 43. A reference voltage is applied to the non-inverting inpt of op amp 42 by a resistor 46 and a voltage divider consisting of resistors 47 and 48. A feedback resistor 49 is connected between the output and the inverting inpt of the op amp, and as discussed more fully hereinafter, the input signal applied to the non-inverting input is such that the output of the op amp is normally high or close to the supply voltage +V (e.g. 22.5 volts). The output of amplifier 42 is connected to the base of transistor 43, and the collector of this transistor is connected to the gate of the SCR. A resistor 51 is connected between the emitter of transistor 43 and ground, and a diode 52 and resistor 53 are connected between the collector and supply line 16. In the preferred embodiment, resistors 51 and 53 are chosen to have values such that the voltage at the collector of transistor 43 and the gate of SCR 41 is on the order of 22 volts when the transistor is turned on.

It will be noted that SCR 41 can be triggered either by an increase in the control signal at the gate or by a decrease in the battery voltage at the cathode.

Means is provided for triggering SCR 41 to deliver a fast charge current to the defibrillator battery. This means includes a normally open push-button switch 56 having a first terminal connected to the supply voltage +V and a second terminal connected to the non-inverting input of an operational amplifier 57 through a capacitor 58. A feedback resistor 59 is connected between the output of op amp 57 and the non-inverting input, and a resistor 61 is connected between this input and ground. A biasing voltage is applied to the inverting input of amplifier 57 by a resistor 62 and capacitor 63 connected to the supply voltage +V. A potentiometer 64 is connected to the output of amplifier 57, and a portion of the output voltage is applied to the inverting input of amplifier 42 by potentiometer 64 and a coupling resistor 66. In the preferred embodiment, the potentiometer is adjusted to make the output of amplifier 42 zero when amplifier 57 begins to conduct. A feedback resistor 67 is connected between the output of amplifier 42 and the non-inverting input of amplifier 57, and as discussed more fully hereinafter amplifier 57 is latched in a conductive state following actuation of switch 56. A light emitting diode (LED) 68 and resistor 69 are connected to the output of amplifier 57 to provide a visual indication when the fast charge current is being delivered to the battery.

SCR 41 is adapted for sensing the voltage on the battery and delivering operating power directly to the defibrillator in the event that the battery is unable to do so. In this regard, it will be noted that the gate of the SCR is normally maintained at a voltage on the order of 22 volts, while the cathode of the SCR is connected to the positive terminal of the battery. In the event that the battery voltage drops below 22 volts by an amount corresponding to the triggering voltage of the SCR, the SCR will begin to conduct. In the preferred embodiment, the SCR requires a trigger voltage on the order of 1 volt, and consequently operating power is delivered to the defibrillator by the SCR in the event that the battery drops below 21 volts.

In order to prevent venting of the battery, means is provided for interrupting the fast charge current when the temperature of the battery reaches a predetermined level. This means includes a silicon diode 71 mounted on a flat metal plate in close thermal contact with all of the cells of the battery. The metal plate has a small thermal resistance and a small thermal capacity, and consequently the temperature of the diode corresponds closely to the temperature of the hottest cell. Suitable silicon diodes have a temperature coefficient on the order of 1 to 2 millivolts per degree Fahrenheit.

Diode 71 is connected in a bridge circuit with a reference diode 72, fixed resistors 73 and 74, and a potentiometer 76. Operating power for the temperature sensing bridge is obtained from the battery, and the output of the bridge is connected to the inverting and non-inverting inputs of amplifier 42 by resistors 77 and 78. In the preferred embodiment, the fast chargecurrent is interrupted when the temperature of the cell is 20° F above the ambient level.

Means is also provided for protecting the defibrillator against damage resulting from excessive charging of the battery. This means includes a transistor 81 having a collector resistor 82 connected to the junction of diode 52 and resistor 53. The conductivity of this transistor is controlled by a voltage proportional to the voltage at output terminal 8. This voltage is applied to the base of the transistor by a voltage divider consisting of a fixed resistor 83 and a potentiometer 84. In the preferred embodiment, potentiometer 84 is adjusted so that transistor 81 is turned on when the output voltage reaches a level on the order of 35 volts.

Means is provided for preventing overloading of Zener diode 19 when the low battery indicator LED 32 and the fast charge indicator LED 68 are both deenergized. This means includes an operational amplifier 86 having a load resistor 87 connected to its output. A reference voltage is applied to the non-inverting input of op amp 86 by a voltage divider consisting of resistors 88 and 89. Input signals are applied to the inverting input by resistors 91 and 92 connected to the outputs of op amps 33 and 57, respectively. If either LED 32 or LED 68 is energized, the signal at the inverting input of op amp 86 will be high, and no current will flow through load resistor 87. If neither of the LEDs is energized, the signal at the inverting input of amplifier 86 will be low, and the current which would flow through an energized LED is absorbed by resistor 87.

Operation and use of the battery charger can be described briefly. It is assumed that the power supply is connected to a suitable source of alternating current, such as 120 volts, and that the charger is connected to a defibrillator and battery, as illustrated. Initially, it is further assumed that the charger is supplying only a trickle charge to the battery. In this situation, LED 28 is energized to indicate that the battery is receiving the trickle charge, and LEDs 32 and 68 are deenergized, indicating that the battery voltage is not below the level set by potentiometer 37 and that the charger is not in the fast charge mode. The output of op amp 57 is zero, making the output of op amp 42 high (e.g. +22.5 volts), holding transistor 43 in a conductive state, and applying a control signal of 22 volts to the gate of SCR 41.

In the event that the battery voltage drops below the sum of the control signal and the threshold voltage of the SCR (e.g. below 21 volts), the SCr will fire, and operating current will be supplied directly to the defibrillator through the SCR. The drop in battery voltage causes the output of op amp 33 to increase, thereby energizing LED 32 to indicate that the battery needs attention. Thus, the charger automatically supplies operating power to the defibrillator in the event that the battery is unable to do so, and it provides a visual indication that the battery voltage is low.

When the battery needs recharging, as indicated by the illumination of LED 32, an operator can initiate the fst charge cycle by depressing switch 56. This provides an increase n the output of op amp 57 and a decrease in the output of op amp 41, illuminating LED 68 and turning off transistor 43. With transistor 43 turned off the voltage at the gate of the SCR increases, firing the SCR to deliver the fast charge current to the battery.

While fast charge current is being delivered to the battery, resistors 59 and 61 apply a voltage on the order of 4 volts to the non-inverting input of op amp 57, and the op amp functions as a level detector having a threshold voltage of 4 volts. The fast charge current continues to be delivered until the temperature of the battery increases about 20° F and the voltage at the output of op amp 42 reaches a level on the order of 4 volts. This voltage is applied to the inverting input of op amp 57 by resistor 67, and when it exceeds 4 volts by a few millivolts, the output of op amp 57 reverts to zero making the output of op amp 42 high and turning on transistor 43. With transistor 43 turned on, the control signal applied to the gate of SCR 41 again increases, turning off the SCR and terminating the fast charge cycle. As long as the battery temperature is 20° F or more above the ambient temperature, the operator cannot return the charger to the fast charge mode by closing switch 56. If the switch is closed before the battery has cooled down, the voltage produced at the output of op amp 42 by the temperature sensor will immediately reutrn the output of op amp 57 to zero, preventing the delivery of further fast charge current to the battery.

In the event that the voltage at output terminal 8 exceeds the level set by potentiometer 84 (e.g. 35 volts) with SCR 41 conducting, transistor 81 will begin to conduct, diverting the gate current from the SCR. With the gate current diverted, the SCR stops conducting, and the current to the battery is interrupted.

The invention has a number of important features and advantages. In addition to providing a trickle charge and a fast charge for maintaining the battery in a charged condition, the charger monitors the battery voltage and automatically delivers operating power directly to the defibrillator if the battery is unable to do so. The battery and defibrillator are protected from damage due to overcharging of the battery, and an operator cannot force the battery to be overcharged.

It is apparent from the foregoing that a new and improved battery charger for defibrillators has been provided. While only the preferred embodiment has been described, as will be apparent to those familiar with the art, certain changes and modifications can be made without departing from the scope of the invention as defined by the following claims.

I claim:

1. In combination, a defibrillator, a battery connected to the defibrillator for supplying operating power thereto, and a charger connected to the battery, said charger comprising: means for delivering a trickle charge current to the battery, means for delivering a fast charge current to the battery for charging the same at a rate faster than the trickle charge, and means responsive to the level of the battery voltage for supplying operating power directly from the charger to the defibrillator in the event that the battery voltage falls below a predetermined level.

2. The combination of claim 1 wherein the battery charger includes means responsive to the temperature of battery for interrupting the fast charge current when the temperature reaches a predetermined level.

3. The combination of claim 1 wherein the battery charger includes means responsive to the battery voltage for interrupting the fast charge current in the event that said voltage reaches a predetermined level.

4. The combination of claim 1 wherein the battery charger includes means for providing a visual indication in the event that the battery voltage drops below a predetermined level.

5. In combination, a defibrillator, a battery connected to the defibrillator for supplying operating power thereto, and a battery charger connected to the battery, said battery charger comprising: a power supply, means for delivering a trickle charge current from the power supply to the battery for maintaining the same in a charged condition, means for providing a control signal having a normal level and a fast charge level, and means responsive to the control signal and to the level of the battery voltage for applying a fast charge current of greater magnitude than the trickle charge current to the battery when the control signal is at the fast charge level and for delivering operating power directly from the power supply to the defibrillator in the event that the battery voltage drops to a predetermined level relative to the normal level of the control signal.

6. The combination of claim 5 wherein the means for applying the fast charge current and delivering operating power comprises a silicon controlled rectifier (SCR).

7. The combination of claim 6 wherein the anode and cathode of the SCR are connected respectively to the power supply and one terminal of the battery and wherein the control signal is applied to the gate of the SCR.

8. The combination of claim 5 further including means responsive to the battery voltage for returning the control signal from the fast charge level to the normal level in the event that the battery voltage reaches a predetermined level.

9. In a battery charger for use with a battery powered defibrillator: a power supply, output terminals for connection to the terminals of a battery connected to the defibrillator, means for delivering a charging current from the power supply to the output terminals for maintaining the battery in a charged condition, switching means including a silicon controlled rectifier (SCR) connected between the power supply and the output terminals for delivering operating current for the defibrillator directly from the power supply to the output terminals, an amplifier, means for applying a reference signal to one input of the amplifier, means including a manually operable switch for applying an input signal to a second input of the amplifier whereby the amplifier has a first output level when the switch is in a first position and a second output level when the switch is in a second position, and a transistor connected between the output of the amplifier and the gate of the SCR whereby the level of the signal applied to the gate of SCR corresponds to the output level of the amplifier, the SCR being actuated when the amplifier output is at the second level.

10. The battery charger of claim 9 further including means responsive to the temperature of the battery for applying an input signal to the second input of the amplifier to return the amplifier output to the first level in the event that the battery temperature exceeds a predetermined level.

* * * * *